United States Patent [19]

Asherman, Jr.

[11] Patent Number: 5,478,333
[45] Date of Patent: Dec. 26, 1995

[54] MEDICAL DRESSING FOR TREATING OPEN CHEST INJURIES

[76] Inventor: Richard E. Asherman, Jr., 3902 Perrin Central, Apt. 908, San Antonio, Tex. 78217

[21] Appl. No.: 207,017

[22] Filed: Mar. 4, 1994

Related U.S. Application Data

[63] Continuation-in-part of Ser. No. 95,047, Jun. 10, 1993, abandoned.

[51] Int. Cl.$^6$ ..................................................... A61F 13/00
[52] U.S. Cl. ........................... 604/304; 128/887; 128/888; 604/307; 604/355
[58] Field of Search ..................................... 128/887, 888; 602/42, 58, 59; 604/122, 175, 247, 318–320, 332, 344, 355, 277, 278, 304, 307, 323, 335, 350; 137/846, 850

[56] References Cited

U.S. PATENT DOCUMENTS

| 3,522,807 | 8/1970 | Millenbach . | |
|---|---|---|---|
| 4,413,621 | 11/1983 | McCracken et al. | 128/156 |
| 4,465,062 | 8/1984 | Versaggi et al. | 128/1 |
| 4,717,382 | 1/1988 | Clemens et al. | 604/122 |
| 5,090,406 | 2/1992 | Gilman | 602/47 |
| 5,160,322 | 11/1992 | Scheremet et al. | 604/122 |
| 5,195,977 | 3/1993 | Pollitt | 604/122 |
| 5,263,922 | 11/1993 | Sova et al. | 128/888 |

FOREIGN PATENT DOCUMENTS

| 3524893 | 1/1987 | Germany | 604/319 |

OTHER PUBLICATIONS

"Heimlich Valve for Chest Drainage", Medical Instrumentation AAMI, vol. 17, No. 1, Jan.–Feb., 1983.
Annals of Emergency Medicine #132, May 1993 edition.

*Primary Examiner*—Randall L. Green
*Assistant Examiner*—Rob Clarke
*Attorney, Agent, or Firm*—Gunn, Lee & Miller

[57] ABSTRACT

A medical dressing for treating open chest injuries, or other injuries that compromise or could possibly compromise the pleural space of the chest cavity. Specifically, a medical dressing used by first responders to treat an open pneumothorax, treat and/or prevent a tension pneumothorax from developing, remove the accumulated blood of a hemothorax or re-inflating a collapsed lung without invasive procedures and in some instances act as a conduit for treating a tension pneumothorax or a collapsed lung with invasive procedures.

9 Claims, 4 Drawing Sheets

MEDICAL DRESSING FOR TREATING OPEN CHEST INJURIES

Continuation-in-part application based on U.S. patent application Ser. No. 08/075,047, filed on Jun. 10, 1993, now abandoned, entitled: Medical Dressing for Treating Open Chest Injuries.

BACKGROUND OF THE INVENTION

1. Field of The Invention

Applicant's invention relates to multi-purpose medical dressings, in particular, dressings for treating open chest injuries or other injuries that compromise, or could possible compromise the pleural space of the chest cavity. Specifically, a medical dressing used by first responders to treat an open pneumothorax, treat or prevent a tension pneumothorax from developing without invasive procedures, evacuate the pooled blood in a hemothorax or re-inflate a collapsed lung without invasive procedures, and, in some instances, act as a conduit for treating a collapsed lung or a tension pneumothorax with invasive procedures.

2. Background Information

Figure 6:
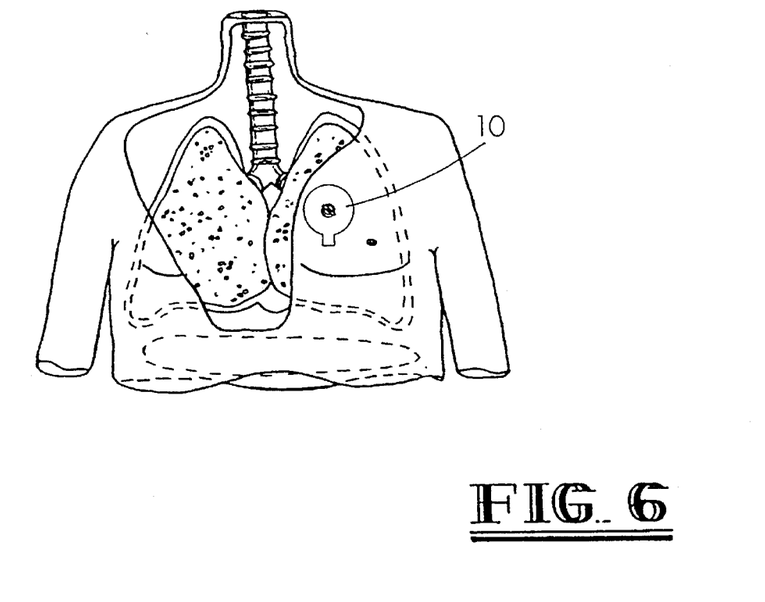
FIG. 6 is a cut-away of the chest showing the chest cavity.

FIG. 6 is a diagram of the chest cavity. When a person is shot or stabbed in the chest, the wound often times penetrates a sufficient distance into the chest cavity to puncture the parietal pleura, visceral pleura, and the lungs. In some cases two wound holes are formed, an entry and an exit hole. A wound hole(s) that penetrates the chest cavity and parietal pleura allows air and/or blood to flow freely into the chest cavity, the pleural space, and possibly the lungs.

The condition wherein air penetrates into the pleural space between the lung and the chest wall through a wound hole in the chest wall is an open pneumothorax. When an open pneumothorax occurs, the normal mechanism by which the lung expands is lost; i.e., the fluid adhesion of the pleural surface of the lung to the pleural surface of the chest wall. Thus, the affected lung does not expand when the patient inhales and respiratory distress becomes severe and possibly fatal. For patients with an open wound to the chest, the severity of the open pneumothorax that develops can be minimized by sealing the open wound via an occlusive bandage prior to transport. The occlusive bandage is used to eliminate air penetrating into the pleural space through the wound hole when the patient inhales. If the intake of air into the pleural space is not entirely eliminated, additional air will be trapped in the pleural space, thus causing the pressure in the affected chest cavity to rise. If the pressure in the chest cavity exceeds normal pressure, blood flow from the heart to the lungs may be halted, with death rapidly following. Thus, it is imperative that when treating an open pneumothorax, that the wound is appropriately sealed in a manner which eliminates air from penetrating into the pleural space through the wound hole.

The current day medical procedures used by first responders to treat an open pneumothorax are occlusive type dressings. For example, (1) petrolatum gauze dressing, (2) a sterilized aluminum foil dressing, or (3) a folded universal dressing placed over the wound. The gauze dressing, foil or universal dressing is taped to the skin on all four sides of the wound. By taping the dressing on all four sides, the first responder is attempting to eliminate air penetrating into the pleural space through the wound. Yet, in most instances, this type of dressing is ineffective. It either (1) does not totally eliminate air entering the pleural space through the wound; (2) eliminates air penetrating into the pleural space through the wound yet does not allow the already trapped air to escape; or (3) a combination of both. These defects could cause a more serious tension pneumothorax to develop which leads to respiratory insufficiency and heart failure. Consequently, a need exists for a method and apparatus for successfully treating an open pneumothorax that can be used by first responders, which totally eliminates the intake of outside air into the pleural space via the wound hole yet allows already trapped air to escape.

In addition to developing a tension pneumothorax by using defective dressings as discussed above, a patient with an open chest wound and a severe lung laceration may also develop a tension pneumothorax in a different manner. For instance, the bandage may have eliminated air from entering the pleural space through the wound hole, yet if lacerated, the lung will continue to leak air into the pleural space. Consequently, every time the patient inhales, more air becomes trapped in the pleural space, causing more pressure to be exerted on the lacerated lung. This increased pressure on the lacerated lung forces the lung to collapse until reduced to a ball 2–3 inches in diameter. At this point of collapse, pressure in the affected chest cavity begins to rise, the collapsed lung is pressed against the heart and the lung on the opposite side, compressing the remaining uninjured lung. If the pressure in the chest cavity exceeds the normal pressure of the blood returning to the heart, blood flow from the heart to the lungs may be halted, with death rapidly following.

To successfully prevent a tension pneumothorax from developing, the air flow into the pleural space via the wound hole must be eliminated, but the air coming from the lacerated lung must be allowed to escape the pleural space via the wound hole. The method of treatment currently used by first responders is the same type of dressing used to treat an open pneumothorax except it is taped on only three sides of the wound. The untaped side of the bandage theoretically allows air to exit the pleural space through the wound hole when the patient exhales. As the patient inhales, the three sided dressing theoretically collapses against the wound, thus prohibiting air from entering the pleural space through the wound hole.

In most instances, three sided dressings are ineffective. Initially, the amount of blood that normally accompanies the chest wound prohibits the tape from securely attaching the dressing to the patient. Secondly, when the petrolatum gauze dressing is opened, it becomes creased, making it less form fitting to the body. Consequently, air can both enter and exit the chest cavity because the petrolatum gauze is not sucked against the wound when the patient inhales. Petrolatum is also necrotizing to the lung tissue. If petrolatum penetrates the wound and contacts the lung tissue, the lung tissue may die. Finally, for less experienced or less trained first responders, their common protocol when treating any type of chest wound is to apply a totally occlusive, four-sided bandage instead of a non-occlusive three-sided dressing. If a four-sided bandage is used in conjunction with a lacerated lung, or an already developing tension pneumothorax, the results can be deadly. Consequently a need exists for a medical dressing for use by first responders that effectively treats both an open pneumothorax and a tension pneumothorax and accordingly does not require the first responder to determine if a three sided or four sided bandage is required.

Other than the above described ineffective three sided or four sided dressings, the only other procedure currently used to treat or prevent a tension pneumothorax from developing is an invasive procedure using a needle thoracentesis (FIG. 10) that may only be performed by highly trained medical professionals. Therefore, a need exists for a method and apparatus for treating or successfully preventing a tension pneumothorax from developing which does not require invasive procedures. The apparatus must allow air to escape from the pleural space, yet not allow air to enter the pleural space through the wound hole.

In some instances, medical personnel having the training to perform a needle thoracentesis are on the scene. A needle thoracentesis is an invasive procedure to immediately decompress a tension pneumothorax. It is performed when a tension pneumothorax has progressed to a point that the affected lung has completely collapsed, putting pressure on the mediastinum, which affects the operation of the heart and the good lung.

The needle thoracentesis procedure consists of taking a large bore catheter, 14 gauge or larger, and inserting it into the second intercostal space in the mid-clavicular line of the patient's chest on the side of the tension pneumothorax. The catheter is inserted until trapped air begins to escape from the plural space. The catheter remains in the chest to allow all pressure to escape. After air stops escaping through the catheter, it is also removed. After the catheter is removed, if a tension pneumothorax begins to again develop, it becomes necessary to repeat the above procedure which is very time consuming and cost ineffective. Furthermore, on the battle field, medics do not have the time to continually repeat the needle thoracentesis on several patients. Consequently, a need exists that would allow a mechanism for the catheter to be maintained in the chest yet, securing the catheter in such a manner that it does not become inoperable and possibly forced into a position harmful to the patient.

In addition to a tension pneumothorax, a patient with a chest wound may also experience a hemothorax. A hemothorax is the presence of blood in the pleural space. The blood in the pleural space may come from lacerated vessels in the chest wall, from lacerated major vessels within the chest cavity itself, or from a lacerated lung. In a hemothorax, the pleural space becomes filled with blood. Normal lung expansion does not occur, and the lung itself is compressed, thus less air is inhaled. In addition, significantly less blood may be available to carry the reduced level of oxygen to the patient's vital organs.

To treat a hemothorax, the blood must be removed from the pleural space to allow the lung to expand to its normal capacity. Current day treatment of a hemothorax by a first responder includes application of an occlusive dressing over the wound, positioning the patient onto the injured side, thus limiting the pooled blood to the wound side of the chest cavity, immediate ventilatory support, administration of oxygen, and immediate transportation to the hospital. Treatment by first responders does not currently include removal of the accumulated blood from the pleural space.

Removal of the blood in the pleural space does not occur until the patient is in the hospital. Once in the hospital, a chest tube is inserted into the wound and negative pressure, i.e. suction, is applied to remove the accumulated blood in the pleural space. If a sufficient quantity of blood accumulates in the pleural space before the patient arrives at the hospital, the lacerated lung may collapse. Therefore, it is imperative that the blood be removed from the pleural space as soon as possible. Consequently, a need exists for a method and apparatus to be used by a first responder for removal of blood in the chest cavity.

An unwanted result of a tension pneumothorax and a hemothorax is a collapsed lung. Currently, a collapsed lung is only re-inflated through invasive procedures in the hospital. First responders at this time do not treat a collapsed lung. If a collapsed lung is not treated, it can lead to further respiratory difficulties in an already traumatized patient. Consequently, a need exists for a method and apparatus for successfully re-inflating a collapsed lung by a first responder.

Finally, medics on the battlefield face dilemmas everyday due to the limited space in a medic's pack. Consequently, when the bandage used to treat often encountered wounds on a battlefield is compact, the compactness increases each wounded soldier's chances of survival. Chest wounds are one of the most encountered injuries on a battlefield. Consequently, a need exists for a small, compact yet efficient bandage that can be used on the battlefield to treat open chest wounds. In addition to being compact, the bandages must require little attention after application, and continue to operate for at least an hour after application due to distances from the battlefield to the nearest care facility.

DESCRIPTION OF THE PRIOR ART

U.S. Pat. No. 4,465,062 entitled "Non-Invasive Seal for a Sucking Chest Wound" issued to Versaggi, et al on Aug. 14, 1984, discloses a rectangular shaped bandage attached to a teflon coated check valve by a flange and ring seal mechanism. The check valve is sealed within a hard plastic dome.

The Versaggi device is an unsatisfactory bandage due to the hard plastic dome. Initially, the plastic dome bars access to the check valve. If the check valve becomes clogged and inoperable, exhaled air will be trapped in the pleural space of the lungs. Through malfunction of the check valve of the Versaggi device, a tension pneumothorax could develop or, if initially treating a tension pneumothorax, further complications such as collapsed lungs and heart failure could be encountered. Thus, death could occur simply because the check valve of the Versaggi apparatus is inaccessible.

Secondly, because of the inaccessibility, the care provider must pay constant attention to the Versaggi device. If the Versaggi device malfunctions, it must be removed and replaced. On the battle field, constant attention is not practical, nor is time available to replace a bandage. On the battle field, medics dress the wounds and send the wounded to the nearest care facility. At times, it may take over an hour for the wounded patient to be transported and treated by personnel with more advanced equipment. Consequently, if the check valve malfunctions and it goes unnoticed, a tension pneumothorax may develop and the person may die because the inoperability of the check valve.

Third, the hard plastic dome also prevents the Versaggi device from being used in conjunction with suction devices or a needle thoracentesis. Consequently, neither a hemothorax nor a collapsed lung could be treated with the Versaggi device. Rather, these life threatening concerns would have to wait until the patient arrived at a hospital or care facility where invasive procedures could be performed.

In addition to accessibility, Versaggi's hard plastic dome raises other problems. For instance, the plastic dome could break during storage and lacerate the base or check valve, thus rendering the Versaggi device inoperable. The plastic dome also precludes use of the Versaggi device on the down side of a patient. The hard plastic will put undue pressure on and around the wound, causing further damage to the traumatized tissue. In the worst case scenario, the patient's weight could break the plastic dome, cutting the patient or lacerating the valve and rendering the device inoperable. Again, if the patient were not being closely attended, the patient could die due to the malfunction.

The manner in which the Versaggi device is constructed makes it even more undesirable. The check valve has a flange at its lower end which fits through a hole in the rectangular bandage. The flange in conjunction with a ring seal maintains the check valve adjacent to the hole in the bandage. If the ring seal and rectangular bandage are not securely joined, air will penetrate the wound hole via the ineffective seal between the ring seal and bandage. Furthermore, the ring seal precludes use of the Versaggi device on large wounds. If the diameter of the wound hole is larger than the diameter of the ring seal, the height of the ring seal will create a space in which air may be trapped between the bandage and the wound which is not within the diameter of the ring seal. The trapped air would continually penetrate the wound and a tight seal would never be perfected between the valve and the wound due to the trapped air above the wound not covered by the ring seal.

Finally, the size of the Versaggi apparatus further limits its use. Current day gauze/aluminum bandages are envelope size and a number of them easily fit into a medic pack or other emergency personnel equipment. The Versaggi apparatus with its plastic dome is approximately 5–10 times thicker than the current day bandages. Just the size difference alone automatically ensures that fewer of the Versaggi devices could be packed than current day bandages. This smaller number would be detrimental to several soldiers on the battle field or individuals who were involved in a situation where numerous other individuals were also injured and received chest wounds.

U.S. Pat. No. 4,717,382 entitled "Non-Invasive Apparatus for Treating a Sucking Chest Wound" issued to Clemens, et al on Jan. 5, 1988, discloses a reusable apparatus comprised of a compartment for collecting fluid positioned beneath a one-way valve. Initially, the Clemens device is impractical and uneconomical. With today's health concerns and rising deaths from AIDS, care providers would not reuse the Clemens device. Consequently, the cost of manufacturing a reusable device far exceeds the one-time use cost.

The manner in which the Clemens device is maintained adjacent to the wound hole is also impractical. The connection (1) takes too long to secure, (2) could easily be shifted away from the wound hole rendering the device inoperable, and (3) a patient may be too large to use the Clemens device.

The Clemens compartment for collecting fluid is also an undesirable feature. It is positioned directly above the wound hole. This position is detrimental to the patient as some of the fluid may be sucked back into the wound when the patient inhales. Furthermore, health concerns teach away from collecting fluids that may contain life threatening contaminants in this manner wherein the health-care provider may contact the body fluid directly when the device is removed.

Like the Versaggi device, Clemens also cannot be used in conjunction with a suction device to treat a hemothorax or a collapsed lung. Although Clemens does allow for an alternative device that can be connected to suction means, this suction is only used to remove the fluid from the fluid holding compartment. Clemens could not be used in conjunction with suction means to aspirate air or fluid from the chest to treat a hemothorax or a collapsed lung because the distance of the catheter from the wound that Clemens' structure requires would prohibit effective suction of the pleural contents. Due to the valve distance from the wound hole, Clemens could also not be used in conjunction with a needle thoracentesis.

Again, like the Versaggi device, the Clemens device also suffers due to its bulkiness. In many instances, i.e., medic bags, space is of the essence. Consequently, the smaller the apparatus, the larger the number available in the war zone. In comparison to the Clemens device, at least 10–15 foil/ gauze dressings could be packed. In a medic's pack on the battle field, this difference could be life endangering to dozens of soldiers. Due to the bulkiness and hardness of the Clemens device, it could also not be used on the downside of a patient for the same reasons as those listed above in relation to Versaggi. Finally, Clemens' inflatable seal can not be used on the battlefield due to the high probability of aeromedical evacuations. Changes in altitude will cause the inflation level to change which could rupture the inflatable seal, rendering the device inoperable.

SUMMARY OF THE INVENTION

This invention finds great utility in treating an open pneumothorax, treating and/or preventing a tension pneumothorax, treating a hemothorax and re-inflating a collapsed lung without invasive procedures, and in some cases acting as a conduit to treat a tension pneumothorax and a collapsed lung with invasive procedures. In accordance with this invention, a one-way air valve is attached to a body attaching means with an adhesive underside. The center of the body attaching means translates into a generally cylindrical duct segment that in use is positioned near and projects outwardly from the wound hole such that the air expelled from the wound hole flows into the duct segment. The interior of the bottom portion of the one-way air valve is attached to the exterior of the duct segment by an adhesive that is capable of being sterilized.

When Applicant's medical dressing is used to treat an open pneumothorax or treat and/or prevent a tension pneumothorax, the duct segment of the body attaching means is positioned over the wound hole so that air escaping from the wound passes through the duct and exits through the one-way valve. The adhesive underside of the body attaching means is attached to the skin surrounding the wound to maintain the medical dressing in place. As the patient exhales, air is forced from the pleural space, through the wound hole, through the duct segment and exits through the air exit end of the one-way valve. The force of the exhaled air causes the sides of the one-way valve to part so that the air may escape through the air exit end. The sides of the one-way valve collapse back against each other after the air is expelled through the air exit end of the one way valve. As the patient inhales, the unique shape of the one-way valve does not allow air to re-enter the wound through the one-way valve. Thus, Applicant's medical dressing acts as an occlusive bandage when the patient inhales, yet as a non-occlusive bandage when the patient exhales.

The medical dressing may also be used to treat a hemothorax. The medical dressing is placed over the wound as discussed above in treating an open pneumothorax or tension pneumothorax. The tip of a suction catheter or other suction producing device is inserted into the one-way valve and duct segment to a position directly above the wound to remove fluid, air or even a blood clot that is blocking the wound hole. In this procedure, the suction catheter does not penetrate the wound hole.

The medical dressing may also be used in conjunction with suction producing devices to re-inflate a lung that has collapsed. Again, the medical dressing is placed over the wound hole as discussed for treating of a pneumothorax. A suction producing device is inserted into the one-way valve. The lung is re-inflated by the negative pressure produced by the suction producing device directly over the wound hole. Again, in this procedure, the suction producing device is not inserted into the wound hole.

Finally, the medical dressing may also be used as a conduit to treat a tension pneumothorax or a collapsed lung with invasive procedures. In this procedure, a catheter is inserted into the second intercostal space in the mid-clavicular line of the patient's chest on the side that the tension pneumothorax has developed. The catheter is inserted until trapped air or blood begins to escape from the pleural space through the catheter. Tile catheter remains in the chest until air stops escaping from the chest. Applicant's medical dressing is applied to the skin surrounding the catheter such that the one-way valve encircles the catheter and provides support to the catheter, protects the catheter from being bumped or moved into a position that would be detrimental to the patient and also assures the catheter will not kink.

The simplicity of Applicant's device assures it is economical and a feasible replacement for the ineffective aluminum/gauze dressings that are currently being used. Furthermore, the size of Applicant's medical dressing assures its use on the battlefield in other medical emergencies wherein space is in limited supply.

DETAILED DESCRIPTION OF THE PREFERRED EMBODIMENT

Figure 1:
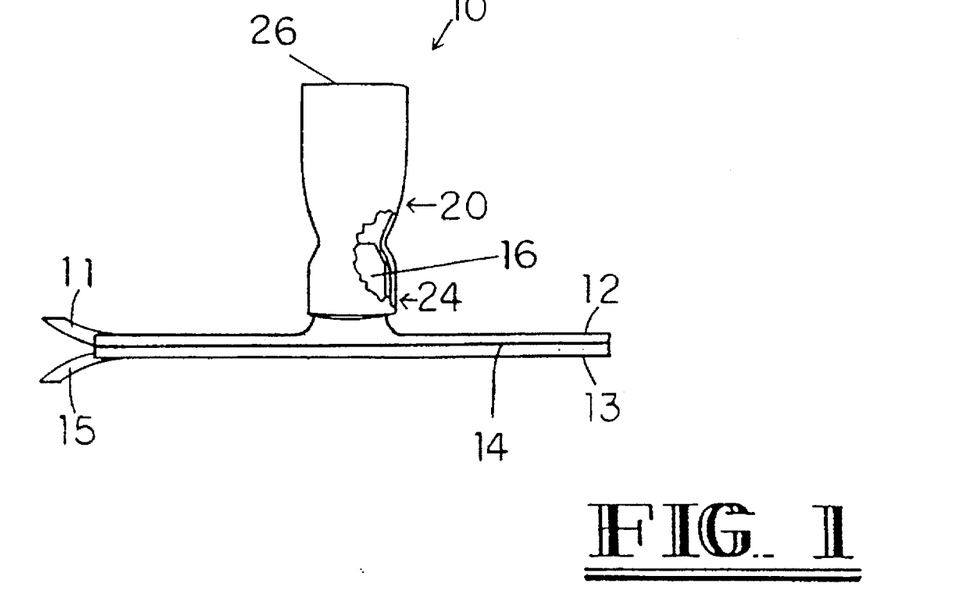
FIG. 1 is a cut-a-way side view of the medical dressing.
Figure 2:
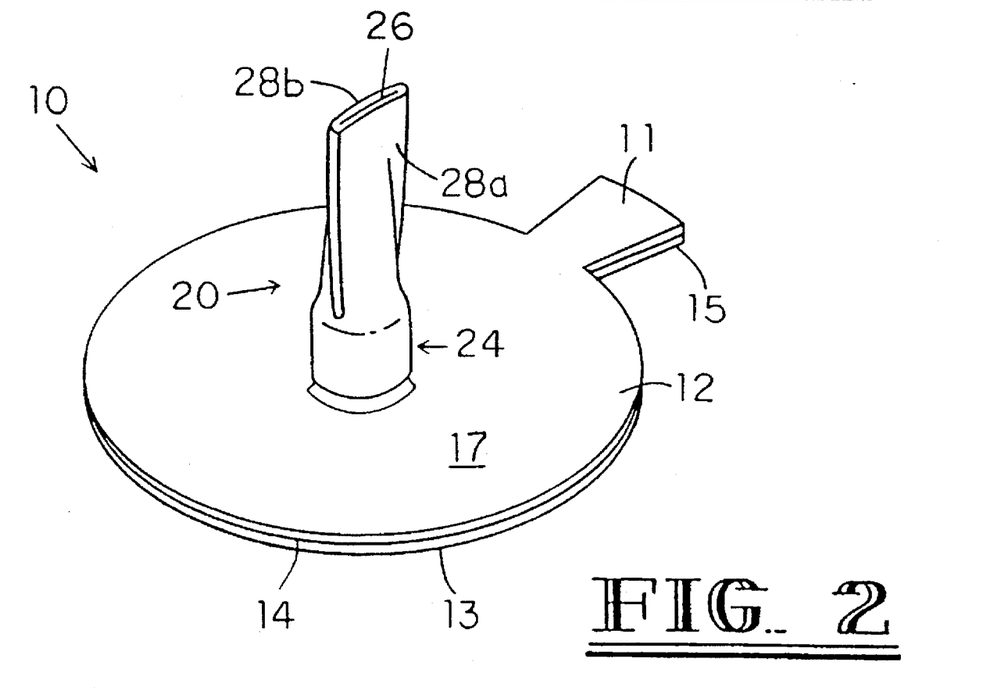
FIG. 2 is a perspective view of the medical dressing.
Figure 3:
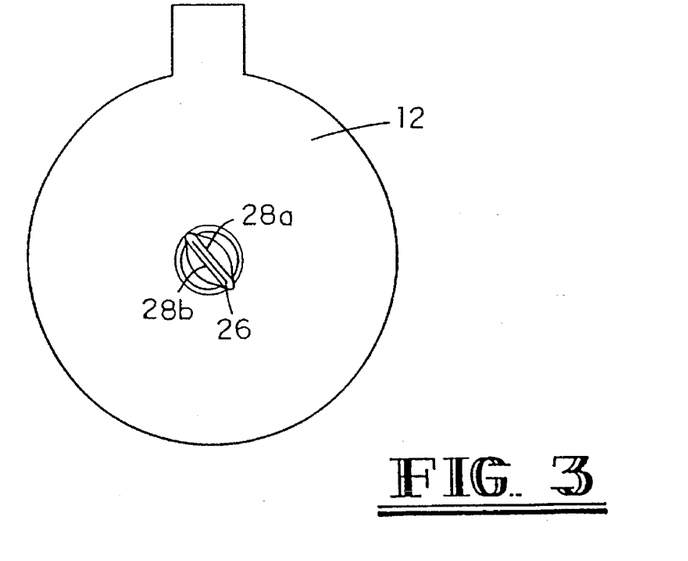
FIG. 3 is a top view of the medical dressing.
Figure 4:
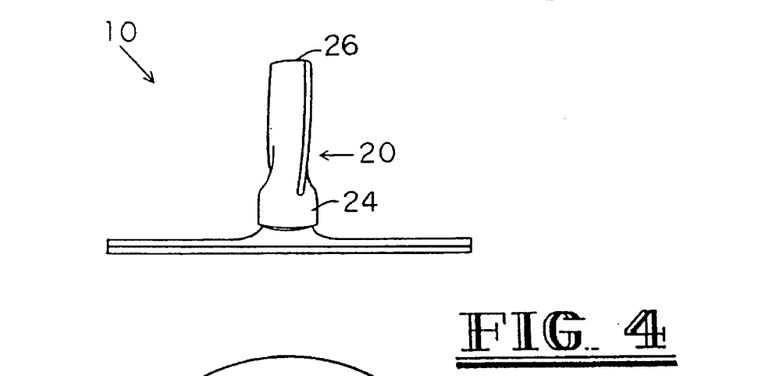
FIG. 4 is a side view of the medical dressing.
Figure 5:
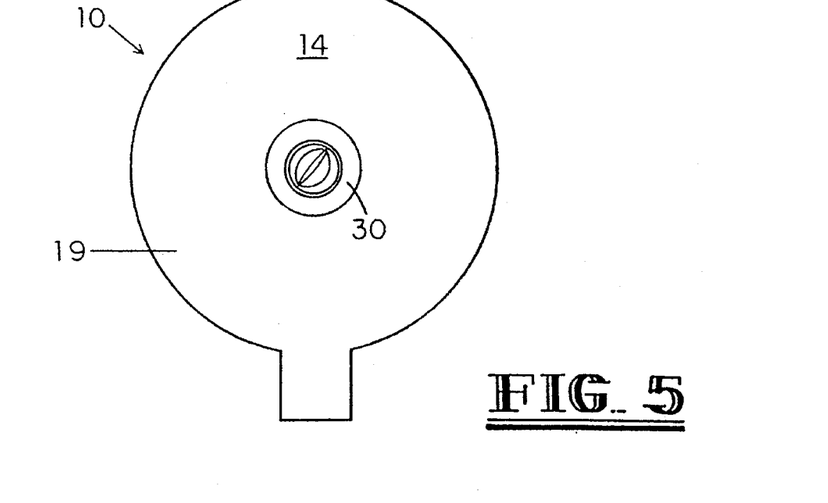
FIG. 5 is a underneath view of the medical dressing.

Referring to FIGS. 1,2 and 3, medical dressing (10) is comprised of one-way valve (20) and body attaching means (12) whose center translates into duct segment (16). Body attaching means (12) has a top side (17) and an underside (19) (See FIG. 5). Referring to FIG. 5, underside (19) of body attaching means (12) includes non-adhesive underside section (30) and adhesive underside section (14). Referring again to FIGS. 1 and 2, tear-away backing (13) covers underside (19) and is attached to adhesive underside section (14). One-way valve (20) has sides (28a–b), lower end (24), and air exit end (26).

Body attaching means (12) has non-adhesive finger hold (11) positioned proximate to non-adhesive finger hold (15) of tear-away backing (13), such that the care provider may pull non-adhesive finger hold (15) away from non-adhesive finger hold (11) to remove tear-away backing (13) from adhesive underside section (14).

Figure 8:
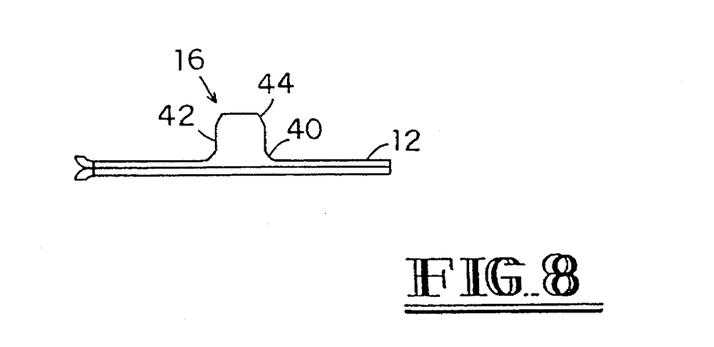
FIG. 8 is a perspective view of the body attaching means without the one-way valve attached.

Referring to FIG. 1, the center of body attaching means (12) translates into duct segment (16). Duct segment (16) allows exhaled air from the wound to pass through body attaching means (12), into one-way valve (20) and through air exit end (26) of one-way valve (20). Referring to FIG. 8, duct segment (16) is comprised of first conical section (40), cylindrical section (42) and second conical section (44). The interior of lower end (24) of one-way valve (20) is attached to the exterior of cylindrical section (42) of duct segment (16) by an adhesive material that is capable of being sterilized.

One-way valve (20) is made of natural rubber, vinyl or other materials which will allow sides (28a–b) of one-way valve (20) to separate when air is expelled from the wound hole through the interior of one-way valve (20), yet allows sides (28a–b) to collapse against each other after the air has been expelled. The preferred material being natural rubber. Body attaching means (12) is made of a flexible polymeric material capable of being sterilized and yet sufficiently rigid such that the sides of duct segment (16) do not collapse against each other during normal operation. The preferred being a styrene block copolymer that is impermeable to both air and fluid such as Kraton 62700 Series Styrene Block Copolymers Product Nos. 2705, 2706 and 2712 by Shell Oil Company. Adhesive underside segment (14) is created by applying most non-air permeable hypo-allergenic adhesives to underside (19) of body attaching means (12), the preferred being a doubled-sided, pressure sensitive adhesive Product No. 1524 by 3M. One-way valve (20) and body attaching means (12) may also be made of clear materials that will enable the care provider to view the wound even after medical dressing (10) is applied.

Body attaching means (12) and one-way valve (20) are constructed of pliable, flexible materials so that medical dressing (10) will adhere to any contour of the human body, including the female breast or a well developed male chest. This is an important feature as current day medical dressings are not normally capable of conforming to these areas. The flexibility of one-way valve (20) also allows medical dressing (10) to be attached to the downside of the patient. Although one-way valve (20) may not open to allow air to be expelled because the patient is lying on the valve, the flexibility of body attaching means (12) and one-way valve (20) of medical dressing (10) assures that the tissue surrounding the wound will not be further traumatized due to hard or unbendable materials putting pressure on the patient's traumatized skin, and Applicant's device will be operable when (1) the patient is not lying on it. The flexibility of one-way valve (20) and the manner in which duct segment (16) of body attaching means (12) is attached to one-way valve (20) assures medical dressing (10) can be packaged in a generally flat, envelope manner. In this manner, medical dressing (10) is either as small as, or possibly smaller, than current day aluminum/gauze dressing. Consequently, in medical situations where supply space is in short demand, at least the same number of medical dressings (10) may be packed as prior art gauze/aluminum dressings. This is specially important in medic packs utilized in war zones or on battle fields.

Medical dressing (10) may also be constructed such that one-way valve (20) and body attaching means (12) are one sheet of pliable plastic and/or other material that is non-permeable yet capable of being sterilized.

To use medical dressing (10) in a non-invasive procedure, the patient's skin around the wound hole is wiped clear of blood and sweat to enhance the adhesive effect of adhesive underside section (14) of underside (19) of body attaching means (12). Tear-away backing (13) is removed from adhesive underside segment (14) of underside (19) of body attaching means (12) by pulling finger hold (11) of body attaching means (12) in an opposite direction from finger hold (15) of tear-away backing (13). Duct segment (16) of body attaching means (12) and one-way valve (20) are positioned over the wound hole (see FIG. 7). This placement assures duct segment (16), one-way valve (20), and air exit end (26) of one-way valve (20) are appropriately positioned over the wound hole. Adhesive segment (14) of underside (19) of body attaching means (12) is then pressed against the skin to assure medical dressing (10) attaches securely to the skin of the patient. As the patient exhales, air is released through duct segment (16) via body attaching means (12) into one-way valve (20) and out through air exit end (26) of one-way valve (20) by the separation of sides (28a–b) of one-way valve (20). After the exhaled air exits through air exit end (26) of one-way valve (20), sides (28a–b) of one-way valve (20) collapse back against each other, thus preventing air from returning through one-way valve (20) when the patient inhales. Additionally, as the patient inhales, sides (28a–b) of one-way valve (20) are sucked against each other, further preventing air from entering the wound through one-way valve (20). If the patient has a multitude of chest wounds, including wounds on the downside, medical dressing (10) is applied to each wound.

Figure 7:
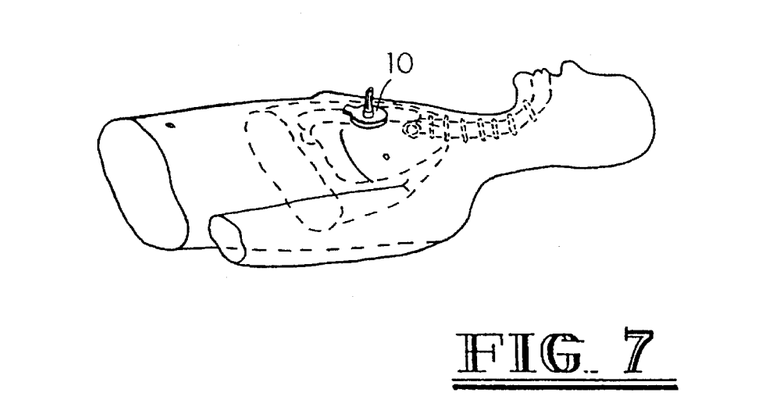
FIG. 7 is a perspective/cut-a-way view of the medical dressing in use.

When the patient exhales, and one-way valve (20) is operable, sides (28a–b) of one-way valve (20) make an audible flutter. If body attaching means (12) and one-way valve (20) are made of a clear material, the care provider may also visually determine if the one-way valve is clogged. Because of the accessibility of one-way valve (20), if one-way valve (20) becomes inoperable due to clogging with blood or other fluids, a suction device can be inserted into one-way valve (20) to immediately remove any material that may be causing one-way valve (20) to be inoperable without breaking the seal created between the wound and one-way valve (20) or requiring replacement of medical dressing (10).

Figure 9:
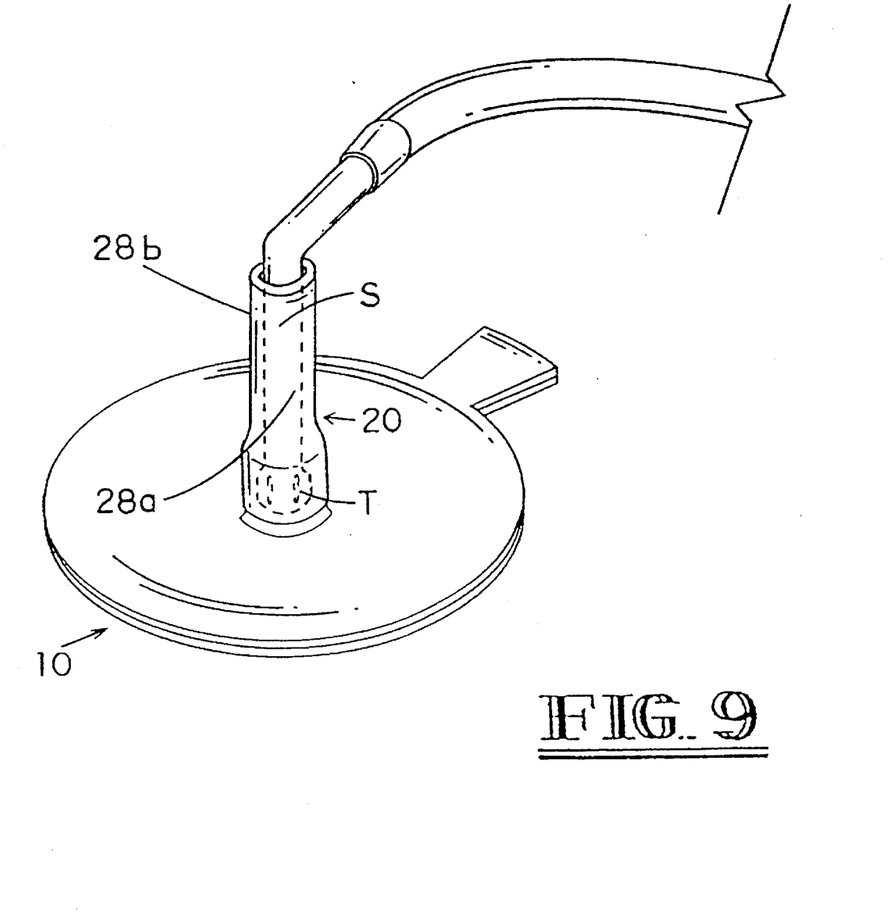
FIG. 9 is a perspective view of the Applicant's medical dressing in conjunction with a suction device.

Referring to FIG. 9, if a hemothorax or a collapsed lung is to be treated without invasive procedures, suction device (S) is inserted into one-way valve (20) and duct segment (16) by forcing sides (28a–b) of one-way valve (20) apart and inserting suction device (S) into one-way valve (20). Tip (T) of suction device (S) is positioned directly above the wound hole. In this manner, suction device (S) removes fluids, air and blood clots which may be on the surface of or being expelled out of the wound hole. If a hemothorax is being treated, the patient may also be turned on the side which has the wound. In this position, blood may drain from the pleural space through the wound hole which suction device (S) may collect.

Figure 10:
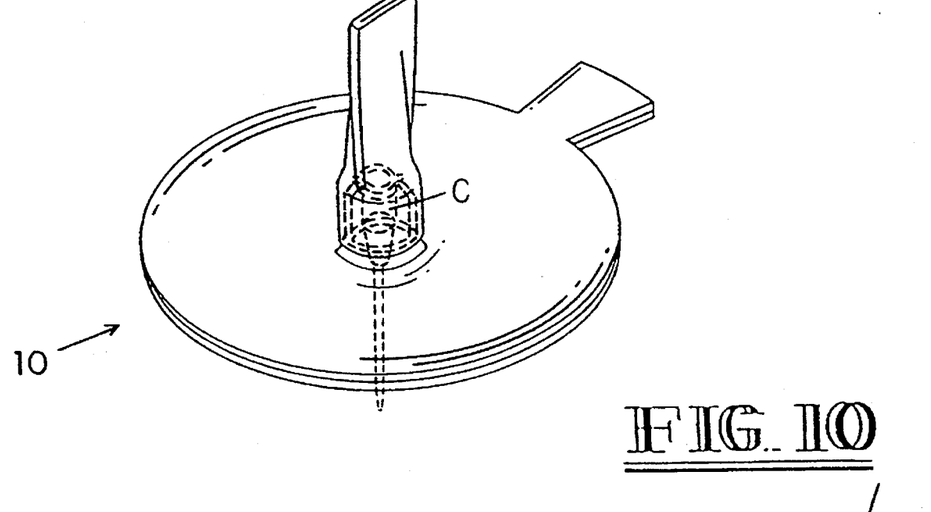
FIG. 10 is a perspective view of the Applicant's medical dressing in conjunction with a catheter.

FIG. 10 illustrates medical dressing (10) being used as a conduit for a catheter (C). If a severe tension pneumothorax or a collapsed lung is to be treated with invasive procedure, the catheter (C) is inserted into the patient's chest near the second intercostal space (between the second and third rib) in the mid-clavicular line (an imaginary line going straight down from the center of the clavicle) of the patient's chest on the side of the tension pneumothorax or collapsed lung until trapped air begins to escape from the pleural space. Catheter (C) remains in the chest until all pressure is relieved. Medical dressing (10) is positioned such that one-way valve (20) and duct segment (16) encircle catheter (C). To use, sides (28a) and (28b) of one-way valve (20) are forced apart and catheter (C) is inserted into one-way valve (20). Adhesive underside segment (14) of underside (19) of body attaching means (12) is then applied to the skin securing medical dressing (10) such that one-way valve (20) of medical dressing (10) supports catheter (C). Catheter (C) can remain in the patient's chest for an unlimited amount of time. Leaving catheter (C) in the lung assures that a crisis situation will not arise again. By using medical device (10), catheter (C) is sufficiently protected and supported such that catheter (C) will not be moved into a position that could be detrimental to the patient.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A medical dressing comprised of:
   a flexible body attaching means with a topside and an underside;
   said body attaching means having a center opening, wherein said body attaching means is drawn into a flexible duct segment extending in the direction of said topside of said body attaching means, said flexible duct segment being generally tubular and having an interior and an exterior side; and
   a flexible single walled one-way valve tube having an interior and an exterior side, a portion of said interior side at a first end of said one-way valve tube is sealed to said exterior side of said flexible duct segment of said body attaching means for enabling passage of air in substantially one direction from said flexible duct segment through said one-way valve tube.

2. The medical dressing of claim 1 wherein said flexible body attaching means and said flexible one-way valve are substantially impermeable to both air and fluids.

3. The medical dressing of claim 2 wherein a portion of said underside of said flexible body attaching means is covered by a double-sided adhesive material, said portion of said underside of said flexible body attaching means covered by said double-sided adhesive being attached to a tear-away backing, said flexible body attaching means further comprising a non-adhesive finger hold, said tear-away backing having a corresponding finger hold adjacent to said finger hold of said body attaching means for assisting in removing said tear-away backing from said underside of said body attaching means.

4. The of claim 2 wherein said flexible, single walled one-way valve tube further comprises a second air exit end with two collapsible walls:
   said second end being opposite said first end of said one-way valve tube attached to said flexible duct segment; and
   said collapsible walls being in a collapsed position when the patient inhales so as to prohibit air from penetrating into the patient's pleural space through the wound hole, and in a non-collapsed position when said patient exhales, to allow the air from said patient's pleural space to be expelled through said flexible one-way valve tube.

5. The medical dressing of claim 4 wherein a portion of said underside of said flexible body attaching means is covered by a double-sided adhesive material, said portion of said underside of said flexible body attaching means covered by said double-sided adhesive being attached to a tear-away backing, said flexible body attaching means further comprising a non-adhesive finger hold, said tear-away backing having a corresponding finger hold adjacent to said finger hold of said body attaching means for assisting in removing said tear-away backing from said underside of said body attaching means.

6. A medical dressing comprised of:
   a flexible, impermeable body attaching means with a top-side, and an underside, said flexible impermeable body attaching means having a center opening drawn into a flexible impermeable duct segment extending in the direction of said top-side of said flexible impermeable body attaching means, said flexible impermeable duct segment being generally tubular and having an interior and an exterior side, said flexible body attaching means further comprising a non-adhesive finger hold, said underside of said flexible body attaching means is covered by a double-sided adhesive material, said portion of said underside of said body attaching means covered by said double-sided adhesive being attached to a tear-away backing, said tear-away backing having a corresponding finger hold adjacent to said finger hold of said body attaching means for assisting in removing said tear-away backing from said underside of said body attaching means;

a flexible, single walled impermeable one-way valve tube having an interior and an exterior side, a portion of said interior side at a first end of said one-way valve tube is sealed to said exterior side of said flexible duct segment of said body attaching means for enabling passage of air in substantially one direction from said flexible duct segment through said one-way valve tube;

said flexible, single walled one-way valve tube further comprising a second end with two collapsible walls;

said second end being opposite said first end of said one-way valve tube attached to said flexible duct segment; and said collapsible walls of said one-way valve tube being in a collapsed position when the patient inhales so as to prohibit air from penetrating into the patient's pleural space through the wound hole and in a non-collapsed position when said patient exhales to allow air from said patient's pleural space to be expelled through said flexible one-way valve tube.

7. A non-invasive method of evacuating accumulated fluid and air from the pleural space of a patient with a chest wound, comprising the steps of:

positioning over said patient's wound hole a medical dressing comprised of a flexible body attaching means having a center opening drawn into a flexible duct segment, said duct segment attached to a flexible, single walled one-way valve tube such that exhaled air passes from said patient's wound hole through said flexible duct segment and said flexible one-way valve tube in substantially one direction;

securing said medical dressing to the skin of said patient surrounding said wound hole;

inserting suction means into said flexible, single walled one-way valve and said flexible duct segment to a position directly over said wound hole;

securing disposal means to said suction means; and engaging said suction means to suck said accumulated fluid and air from said pleural space into said disposal means attached to said suction means.

8. The method of claim 7 further comprising the step of:

positioning said patient on said patient's side having said wound hole such that said fluid drains out of said pleural space through said wound hole.

9. A method of treating a tension pneumothorax, comprising the steps of:

inserting a catheter into the side of the chest of the patient having a wound hole to allow for trapped air to be expelled from the pleural space of said patient;

positioning over said catheter a medical dressing comprised of a flexible body attaching means having a center opening drawn into a flexible duct segment, said flexible duct segment attached to a flexible, single walled one-way valve tube to protect said catheter from moving in a manner detrimental to said patient; and securing said medical dressing to the skin of said patient surrounding said catheter.

* * * * *